United States Patent [19]

Rosso Di San Secondo et al.

[11] Patent Number: 5,721,235
[45] Date of Patent: Feb. 24, 1998

[54] PHARMACEUTICAL COMPOSITION CONTAINING BROMOCRYPTINE AND USE OF SAME FOR ACQUIRED IMMUNODEFICIENCY STATES

[75] Inventors: Vittorio Edmondo Maria Rosso Di San Secondo, Via Passo di Brizio, 6 - 20148, Milan, Italy; Marc E. Freeman; Cheryl Fitch, both of Tallahassee, Fla.; Alina Aniasi; Girolamo Sirchia, both of Milan, Italy

[73] Assignees: Vittorio Edmondo Maria Rosso Di San Secondo, Milan, Italy; Florida State University, Tallahassee, Fla.

[21] Appl. No.: 551,783

[22] Filed: Nov. 7, 1995

[30] Foreign Application Priority Data

Nov. 8, 1994 [IT] Italy .................................. MI94A2253

[51] Int. Cl.⁶ .................................................. A61K 31/495

[52] U.S. Cl. ............................................................. 514/250
[58] Field of Search ................................................. 514/250

[56] References Cited

PUBLICATIONS

Stravoraavdi et al 1991, J of Interfermer Res, vol. 11 (1) pp. 49–51.
Figuernoa et al 120 CA 3213256 1994.
Larson et al 109 CA 6688W 1988.
Merle Index 10th Ed 1983 # 1386.

*Primary Examiner*—Russell Travers
*Attorney, Agent, or Firm*—Hedman, Gibson & Costigan, P.C.

[57] ABSTRACT

The following description refers to a pharmaceutical composition containing bromocryptine and the use of same for the treatment of acquired immunodeficiency states.

4 Claims, No Drawings

PHARMACEUTICAL COMPOSITION CONTAINING BROMOCRYPTINE AND USE OF SAME FOR ACQUIRED IMMUNODEFICIENCY STATES

1. SUMMARY

The present invention relates to a pharmaceutical composition containing bromocryptine which is useful for the treatment of acquired immunodeficiencies.

2. STATE OF THE ART

Bromocryptine (BC), or 2-bromoergocryptine, is a well known product of formula $C_{32}H_{40}BrN_5O_5$, whose dopaminergic properties have been extensively described. On account of said properties, BC is generally used in clinical practice as an inhibitor of the secretion of prolactin (PRL) by the pituitary gland, significantly to reduce the blood levels of said hormone in case of hyperprolactinaemia.

However, it has recently been found that BC, probably due to its ability to inhibit the hypophyseal prolactin production, can potentiate the immunosuppressive activity of cyclosporin A (CsA), potent suppressor of cell mediated immune response, which is used in transplantation to prevent rejections.

3 DETAILED DESCRIPTION OF THE INVENTION

It has surprisingly been found that BC, administered in combination with anti-lymphocytic antiserum (ALS) which is also a potent suppressor of cell mediated immune response used in transplantation to prevent rejections, brings about a potentiation of the immune response, which astonishingly becomes normal again. Considering the ever increasing spread of acquired immunodeficiencies, either iatrogenic (e.g. in the course of transplant or cancer) or ensuing vital diseases, e.g. AIDS, the present invention clearly is of the upmost importance for human therapy.

It has also been found that BC doses suitable for normalizing the immune response in an immunosuppressed animal range from 1 to 50 mg/kg/die, preferably from 3 to 6 mg/kg/die, depending on the gravity of the situation.

BC is preferably administered by injection, in combination with the usual diluents, excipients and vehicles.

A treatment of 10 to 20 days was found to be enough for reestablishing a normal immune response.

With a view to proving the ability of the pharmaceutical compositions based on BC of the present invention to reestablish the immune system functions, studies were conducted to determine the effect of BC on skin transplant rejection in mice immunosuppressed by treatment with ALS.

Said experimental model is appropriate since transplant rejection is a typical immune response of T cells, following the activation of Th1 cells, and ALS is a potent antiserum capable of inducing a generalized immunodeficiency. Clearly, ALS prolongs the rejection time, while the immunostimulating action of BC, which inexplicably appears in this particular situation of acquired immunosuppression, tends to shorten the rejection times.

DETAILED DESCRIPTION OF THE REJECTION TEST

Female mice C57BL/6 and C3H/He were used as recipients and donors respectively: skin transplants were carried out as described by Billingham and Medawar, J. Exp. Biol., 28, 385 (1951) and modified according to Rosso di San Secondo et al., Transplant. Proc., 26, 6 (1994) 3221–3222.

All solutions were administered s.c. starting 2 days before the surgical operation, according to the following protocol.

Bromocryptine (Sigma Chemical Co., St. Louis) was solubilized in 100% ethanol and further diluted in 500 ug/mL saline solution. The final concentration in ethanol was 12%. 5mg/kg of so diluted BC was injected once a day for the overall experiment.

ALS was prepared as described by V. E. M. Rosso di San Secondo et al., J. Immunol., 122, 1658 (1979).

Splenocytes from mice C57BL/6, transplanted with skin from mice C3H/He, were used as a source of mononucleate cells for the sensibilization of rabbits producing immune antibodies, and DEAE-purified IgG were used as a source of ALS. Four doses of ALS (0.1 mL) with 1:100 lymphocytotoxic potency were injected on alternate days.

Table I shows the data obtained with transplanted mice which were administered BC and which were either treated or untreated with ALS; as may be seen, BC-treated mice and controls show analogous transplant rejection times, whereas ALS-treated mice, due to the aforementioned reasons, exibit much longer rejection times. However, when transplanted ALS-treated mice are administered BC, the immune response turns to normal values and the rejection time is analogous to that of controls. Evidently, BC can counteract ALS potent immunosuppressive effect.

TABLE I

| Treatment | Mice No. | Graft Survival time (days) |
|---|---|---|
| Controls | 6 | 8.0 ± 1.4 |
| BC | 7 | 8.5 ± 1.2 |
| ALS | 7 | 13.5 ± 1.2 |
| ALS/BC | 7 | 8.0 ± 1.0 |

In an attempt to identify a possible mechanism of action explaining the unexpected effect of BC administration to ALS-treated animals—a direct action of BC on ALS being excluded—the variation of PRL concentrations vs. the magnitude of the immune response was studied. As known, in fact, PRL increases the immune response by stimulating the differentiation and proliferation of immune cells.

As may be seen in Table II, treatment with ALS and BC raises the values of blood PRL much above the normal values (69.0 vs. 47.4). Considering the role of PRL in normalizing the immune response deficit, the data reported herein strongly suggest a role for PRL in determining the immune response switch from deficit to normal values.

TABLE II

| Treatment | Mice No. | Prolactinaemia (ng/mL) |
|---|---|---|
| Controls | 6 | 47.4 ± 13.5 |
| BC | 7 | 23.4 ± 4.3 |
| ALS | 7 | 31.0 ± 7.3 |
| ALS/BC | 7 | 69.0 ± 4.3 |

This finding too is extremely unexpected in consideration of the well known inhibitory action of BC on PRL pituitary secretion, which is also confirmed by our results. In fact, compared with controls, PRL in mice treated only with BC is clearly lower (23.4 vs. 47.4).

Furthermore, the hypothesis that the normalization of the immune response, probably ensuing a strong stimulation of PRL production, be caused by a potentiation of the immune response, may also be inferred from the very high splenic index in transplanted and BC-and ALS-treated mice (Table III). The splenic index (spleen weight/body weight× 100) is generally regarded as a measure of the intensity of cell mediated immune response, as it reflects a marked proliferation of immunocytes of peripheral lymphoid organs.

As already mentioned, the activity of BC on the immune system was in any case verified in suffers with immunodeficiency induced by drugs or by viruses: this is an undoubted fact, indipendent of and absolutely not bound to any kind of interpretation one tries to give to the phenomenon, which is certainly surprising and unexpected "a priori".

TABLE III

| Treatment | Mice No. | Splenic index |
|-----------|----------|---------------|
| Controls  | 6        | 0.44          |
| BC        | 7        | 0.49          |
| ALS       | 7        | 0.35          |
| ALS/BC    | 7        | 0.98          |

The dose rates of 5 mg/kg/die used in tests on animals were found to be optimal also for humans, within the widest range indicated above.

The therapeutic compositions of the present invention may obviously contain any amount of BC, suitably diluted and mixed, if necessary, with other active ingredients already known. However, the preferred compositions contain 0.1 mg to 1 g of BC and allow the treatment of any suffer with acquired immunodeficiency of any origin.

We claim:

1. A method of treating acquired immune deficiencies in an immunosuppressed host, said method comprising administering to said host 1–50mg/kg/day of bromocryptine.

2. A method as defined in claim 1 wherein the immunosuppressed host is immunosuppressed by an iatrogenic vector.

3. A method as defined in claim 1 wherein the immunosuppressed host is immunosuppressed by a viral agent.

4. A method as defined in claim 3 wherein the immunosuppressed host is immunosuppressed by acquired immune deficiency syndrome.

* * * * *